United States Patent
Min

(10) Patent No.: US 10,668,289 B2
(45) Date of Patent: Jun. 2, 2020

(54) METHOD AND DEVICE FOR CONTROLLING RATE ADAPTIVE PACING BASED ON HEART SOUNDS

(71) Applicant: PACESETTER, INC., Sytlmar, CA (US)

(72) Inventor: Xiaoyi Min, Camarillo, CA (US)

(73) Assignee: Pacesetter, Inc., Sylmar, CA (US)

( * ) Notice: Subject to any disclaimer, the term of this patent is extended or adjusted under 35 U.S.C. 154(b) by 132 days.

(21) Appl. No.: 16/034,254

(22) Filed: Jul. 12, 2018

(65) Prior Publication Data

US 2020/0016410 A1  Jan. 16, 2020

(51) Int. Cl.
| | |
|---|---|
| *A61N 1/36* | (2006.01) |
| *A61N 1/365* | (2006.01) |
| *A61N 1/39* | (2006.01) |
| *A61N 1/362* | (2006.01) |

(52) U.S. Cl.
CPC ....... *A61N 1/36514* (2013.01); *A61N 1/3627* (2013.01); *A61N 1/36521* (2013.01); *A61N 1/3956* (2013.01)

(58) Field of Classification Search
CPC .............. A61N 1/36514; A61N 1/3627; A61N 1/36521; A61N 1/3956; A61B 5/02
See application file for complete search history.

(56) References Cited

U.S. PATENT DOCUMENTS

| | | | |
|---|---|---|---|
| 7,139,609 B1 * | 11/2006 | Min | ........................ A61B 5/02 607/17 |
| 7,702,390 B1 | 4/2010 | Min | |
| 7,778,706 B1 | 8/2010 | Min | |
| 8,442,634 B2 | 5/2013 | Min et al. | |
| 8,565,880 B2 | 10/2013 | Dong et al. | |
| 2004/0147966 A1 | 7/2004 | Ding et al. | |

(Continued)

FOREIGN PATENT DOCUMENTS

WO   2017074999 A1   5/2017

OTHER PUBLICATIONS

Extended European Search Report for corresponding EP Application No. 18186494.3 dated Oct. 8, 2018.

*Primary Examiner* — Eric D. Bertram

(74) *Attorney, Agent, or Firm* — The Small Patent Law Group LLC; Dean D. Small

(57) ABSTRACT

A method and system are provided for controlling an adaptive pacing therapy using an implantable medical device (IMD). The method provides electrodes that are configured to be located proximate to an atrial (A) site, left ventricular (LV) site and right ventricular (RV) site of the heart. The method utilizes one or more processors to perform obtaining an intra-atrial conduction interval (IACI-$LV_{PROX}$) between an atrial event and intrinsic conduction at an LV site that is proximal to a sinoatrial (SA) node and obtaining timing of a first heart sound S1. The processors determine whether the S1 occurs after the IACI-$LV_{PROX}$, and calculates an S1-conduction lag $\Delta S1\_C$ between the IACI-$LV_{PROX}$ and the first heart sound S1. The processors set an atrial-ventricular pacing (AV) delay based on the IACI-$LV_{PROX}$ and the $\Delta S1\_C$. The processors deliver a pacing therapy based on the AV delay.

20 Claims, 7 Drawing Sheets

(56) References Cited

U.S. PATENT DOCUMENTS

| | | |
|---|---|---|
| 2004/0193223 A1 | 9/2004 | Kramer et al. |
| 2005/0209649 A1 | 9/2005 | Ferek-petric |
| 2006/0047320 A1 | 3/2006 | Ding et al. |
| 2006/0235481 A1 | 10/2006 | Fogoros et al. |
| 2008/0269826 A1 | 10/2008 | Lian et al. |
| 2010/0069987 A1 | 3/2010 | Min et al. |
| 2010/0145405 A1 | 6/2010 | Min et al. |
| 2010/0222834 A1 | 9/2010 | Sweeney et al. |
| 2011/0098772 A1 | 4/2011 | Min |
| 2011/0137369 A1 | 6/2011 | Ryu et al. |
| 2012/0165892 A1 | 6/2012 | Min et al. |
| 2017/0119273 A1* | 5/2017 | Thakur ................ A61B 5/4836 |
| 2020/0046312 A1* | 2/2020 | Min ................... A61N 1/36514 |

\* cited by examiner

METHOD AND DEVICE FOR CONTROLLING RATE ADAPTIVE PACING BASED ON HEART SOUNDS

BACKGROUND

Embodiments of the present disclosure generally relate to methods and devices for controlling rate adaptive pacing.

Clinical studies related to cardiac pacing have shown that a select (e.g., optimal) atrio-ventricular pacing delay (AV delay) can improve cardiac performance. However, the select AV delay depends on a variety of factors that may vary over time. For example, what is "optimal" may vary over time. An optimization of AV/PV pacing delay may occur at implantation and sometimes, re-optimization may occur during a follow-up consultation. While such optimizations are beneficial, the benefits may not be long lasting due to changes In various factors related to device and/or cardiac function.

Various systems and methods are provided for allowing an implantable medical device (IMD) to determine and/or adjust atrio-ventricular (AV/PV) delays and/or interventricular (VV) pacing delays so as to help maintain the pacing delays at select values. In particular, techniques have been set forth for exploiting various interventricular conduction delays to determine optimal AV/PV/VV pacing delays. Techniques have also been set forth for exploiting the VV delays to determine which ventricles should be paced—the left ventricle (LV), the right ventricle (RV), both ventricles, or neither.

Other techniques have been set forth for determining AV/PV delays based on inter-atrial conduction intervals and interventricular conduction intervals. In particular, see U.S. Pat. No. 7,248,925, to Bruhns et al., entitled "System and Method for Determining Optimal Atrioventricular Delay based on Intrinsic Conduction Delays," which is fully incorporated by reference herein.

More recently, systems have been proposed to provide rate adaptive adjustment of the PR and AR delays using sensed and paced atrial signals durations, activity responsive optimal PV/AV and VV delays etc. However, an opportunity remains to continue to improve mechanisms for adjusting rate adaptive therapies.

SUMMARY

In accordance with embodiments herein, a method for controlling an adaptive pacing therapy using an implantable medical device (MD) is provided. The method provides electrodes that are configured to be located proximate to an atrial (A) site, left ventricular (LV) site and right ventricular (RV) site of the heart. The method utilizes one or more processors to perform obtaining an intra-atrial conduction interval ($IACI\text{-}LV_{PROX}$) between an atrial event and intrinsic conduction at an LV site that is proximal to a sinoatrial (SA) node and obtaining timing of a first heart sound S1. The processors determine whether the S1 occurs after the $IACI\text{-}LV_{PROX}$, and calculates an S1-conduction lag $\Delta S1\_C$ between the $IACI\text{-}LV_{PROX}$ and the first heart sound S1. The processors set an atrial-ventricular pacing (AV) delay based on the $IACI\text{-}LV_{PROX}$ and the $\Delta S1\_C$. The processors deliver a pacing therapy based on the AV delay.

Optionally, the AV delay may be based on a sum of the $IACI\text{-}LV_{PROX}$ and a percentage (%) of the $\Delta S1\_C$ as follows: AV delay=$IACI\text{-}LV_{PROX}$+%*$\Delta S1\_C$. The determining may comprise determining whether a select point in the S1 occurs after an end of the $IACI\text{-}LV_{PROX}$. The obtaining the timing of the S1 may further comprise obtaining the timing of mitral valve closure based on the S1. The setting the AV delay based on the $\Delta S1\_C$ may further comprise setting the AV delay to avoid delivering a ventricular pacing pulse of a pacing therapy based on the AV delay before a mitral valve closes between the LV and left atrium.

Optionally, the method may comprise measuring a pacing latency PL between a paced event, delivered at the LV site, and an evoked response, sensed at the LV site and may subtract the PL from the AV delay. The setting may further comprise setting the AV delay independent of the S1-conduction lag $\Delta S1\_C$ when the first heart sound St occurs before the end time of the $IACI\text{-}LV_{PROX}$. The delivering the pacing therapy may comprise delivering a biventricular (BiV) pacing therapy. The method may switch from the BiV pacing therapy to a left univentricular pacing therapy that may deliver pacing stimulation at one or more left ventricular sites and may not deliver any pacing stimulation to any right ventricular sites when the first heart sound S1 occurs before the end time of the $IACI\text{-}LV_{PROX}$. The method may identify a patient active state and may perform the setting operation only when in the patient active state.

In accordance with embodiments herein, a system controlling an adaptive pacing therapy using an implantable medical device (IMD) is provided. The system comprises electrodes that are configured to be located proximate to an atrial (A) site, left ventricular (LV) site and right ventricular (RV) site of the heart. Memory stores program instructions. One or more processors are configured to implement the program instructions to perform obtaining an intra-atrial conduction interval ($IACI\text{-}LV_{PROX}$) between an atrial event and intrinsic conduction at an LV site that is proximal to a sinoatrial (SA) node. The processors obtain timing of a first heart sound S1 and determine whether the S1 occurs after the $IACI\text{-}LV_{PROX}$. The processors calculate an S1-conduction lag $\Delta S1\_C$ between the $IACI\text{-}LV_{PROX}$ and the first heart sound S1 and set an atrial-ventricular pacing (AV) delay based on the $IACI\text{-}LV_{PROX}$ and the $\Delta S1\_C$. The processors deliver a pacing therapy based on the AV delay.

Optionally, the AV delay may be based on a sum of the $IACI\text{-}LV_{PROX}$ and a percentage (%) of the $\Delta S1\_C$ as follows: AV delay=$IACI\text{-}LV_{PROX}$+%*$\Delta S1\_C$. The one, or more, processors may be further configured to determine whether a select point in the S1 occurs after an end of the $IACI\text{-}LV_{PROX}$. The one, or more, processors may be configured to obtain the timing of mitral valve closure based on the S1. The one, or more, processors may be configured to set the AV delay based on the $\Delta S1\_C$ in a manner to avoid delivering a ventricular pacing pulse of a pacing therapy based on the AV delay before a mitral valve closes between the LV and left atrium. The one, or more, processors may be further configured to measure a pacing latency PL between a paced event, delivered at the LV site, and an evoked response, sensed at the LV site; and subtract the PL from the AV delay.

Optionally, the one or more processors may be further configured to set the AV delay independent of the S1 conduction lag $\Delta S1\_C$ when the first heart sound S1 occurs before the end time of the $IACI\text{-}LV_{PROX}$. The one or more processors may be configured to deliver a biventricular (BiV) pacing therapy. The one or more processors may be further configured to switch from the BA/pacing therapy to a left univentricular pacing therapy that may deliver pacing stimulation at one or more left ventricular sites and may not deliver any pacing stimulation to any right ventricular sites when the first heart sound S1 occurs before the end time of the $IACI\text{-}LV_{PROX}$. The one or more processors may be further configured to identity a patient active state and may perform the setting operation only when in the patient active state.

Figure 1:
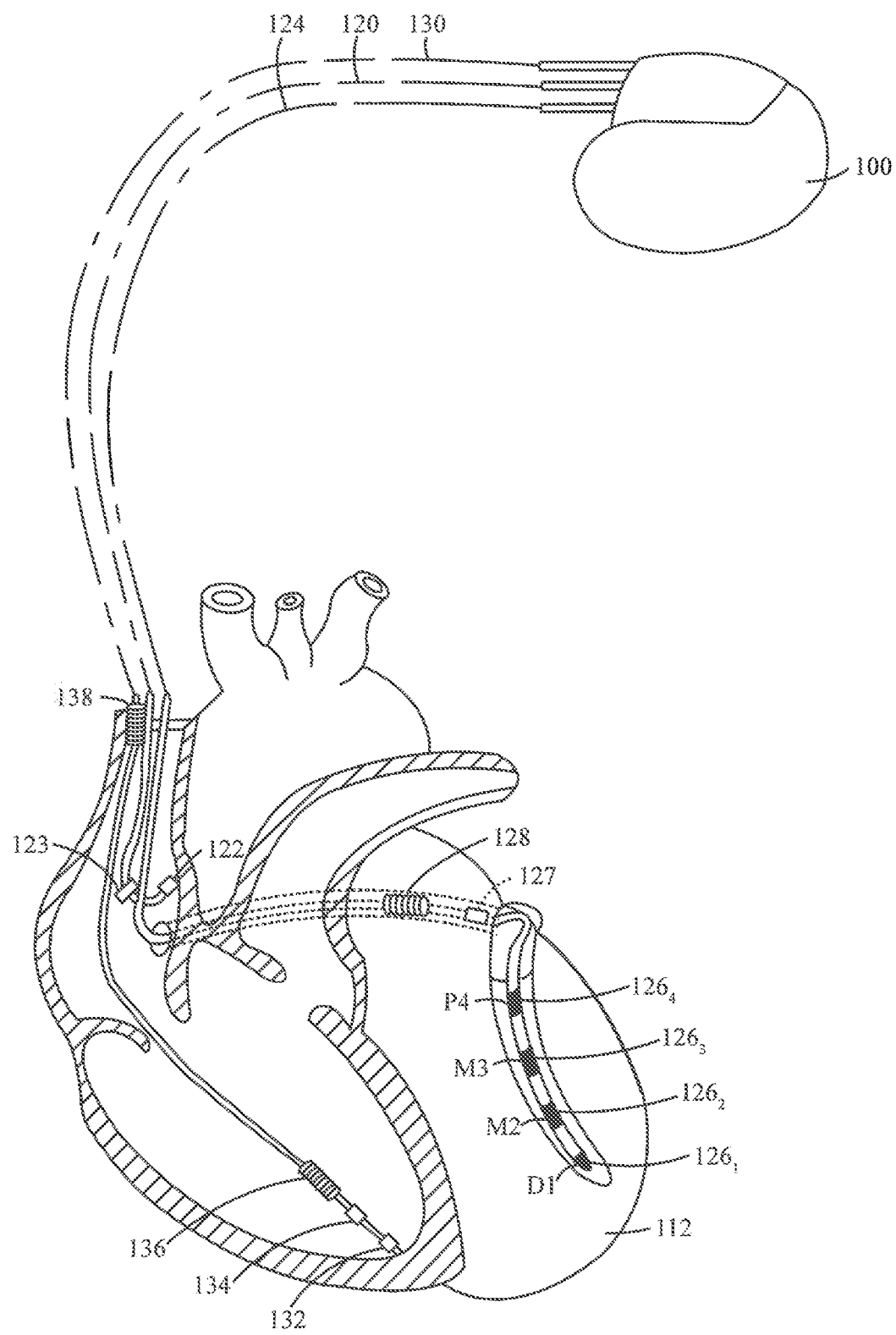
FIG. 1 illustrates an exemplary IMD formed in accordance with embodiments herein.

DETAILED DESCRIPTION it will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "pacing/sensing electrode" refers to an electrode that is controlled and utilized by an implantable medical device and/or external programmer to perform both delivery of pacing pulses at a site and sensing of cardiac signals at the same site.

The term "non-pacing/sensing electrode" refers to an electrode that is controlled and utilized only for sensing operations. The non-pacing-sensing electrode may be on a lead coupled to a lead-based implantable medical device and/or external programmer to perform sensing of cardiac signals at the corresponding site, and is not controlled or utilized to deliver pacing pulses. The non-pacing-sensing electrode may be on a leadless implantable medical device that uses the electrode to perform sensing of cardiac signals at the corresponding site, and does not use the electrode to deliver pacing pulses.

The terms "atrial-ventricular delay", "AV delay" and "AVD" refer to a pacing parameter that is set as a time delay between an occurrence of an intrinsic or paced event in an atria and a time at which the IMD will deliver a pacing pulse in a right ventricle (RV) or a left ventricle (LV), unless an intrinsic ventricular event occurs earlier.

The terms "intra-atrial conduction interval" and "IACI" refer to a time interval experienced between an occurrence of an end of an intrinsic or paced event in an atria and a beginning of a related evoked response as measured at a proximal left ventricular site. The IACI may also be referred to by the abbreviation $IACI\text{-}LV_{PROX}$, to indicated that the conduction interval is measured at a proximal LV sensing site.

The terms "left monoventricular pacing" ("LMV pacing"); "left univentricular pacing" ("WV pacing"); and "left ventricular only pacing" ("LV only pacing") are used interchangeably to refer to pacing therapies that deliver pacing stimulation at one, or more, left ventricular sites and do not deliver any pacing stimulation to any right ventricular sites. The terms "left monoventricular pacing" ("LMV"); "left univentricular pacing" ("LUV"); and "LV only pacing" include therapies that deliver atrial pacing, but do not include biventricular pacing therapies.

Embodiments may be implemented hi connection with one or more implantable medical devices (IMDs). Non-limiting examples of IMDs include one or more of implantable lead-based or leadless therapy devices. For example, the IMD may represent a pacemaker, cardioverter, cardiac rhythm management device, defibrillator, whether lead-based or leadless. For example, the IMD may include one or more structural and/or functional aspects of the device(s) described in U.S. Pat. No. 9,216,285 "Leadless Implantable Medical Device Having Removable And Fixed Components"; U.S. Pat. No. 8,442,634 "Systems and Methods for Controlling Ventricular Pacing in Patients with Long Inter-Atrial Conduction Delays"; and/or U.S. Pat. No. 8,923,965 "Systems and Methods for Optimizing AV/VV Pacing Delays Using Combined IEGM/Impedance-Based Techniques for use with Implantable Medical Devices"; U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are hereby incorporated by reference. Additionally, or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cave. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, IMD 100 is coupled to a multi-pole LV lead 124 designed for placement in the "CS region" via the CS OS for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 124 is designed to receive atrial and ventricular cardiac signals and to deliver left ventricular pacing therapy using a set of four left ventricular electrodes $126_1$, $126_2$, $126_3$, and $126_4$ (thereby providing a quadrupole lead), left atrial pacing therapy using at least a left atrial ring electrode 127, and shocking therapy using at least a left atrial coil electrode 128 implanted on or near the left atrium. In other examples, more or fewer LV electrodes are provided. Although only three leads are shown, it should be understood that additional leads (with one or more pacing, sensing and/or shocking electrodes) might be used and/or additional electrodes might be provided on the leads already shown, such as additional electrodes on the RV lead.

In accordance with embodiments herein, methods and devices are provided that adapt/tailor the parameters of the IMD for a heart failure patient during exercise. The methods and devices measure an intra-atrial conduction interval (IACI-LV$_{PROX}$) from a paced or sensed atrial event to an intrinsic LV event sensed at a proximal/first LV sensing site. The methods and devices also measure a first heart sound S1, such as utilizing an accelerometer in the IMD. Heart Failure (HF) patients exhibit different intra-atrial conduction interval responses relative to the S1 heart sound during exercise. It is desirable to adjust the pacing parameters to avoid pacing at a time that would cause the left ventricle to push blood from the LV back into the left atria (LA).

Embodiments herein avoid the foregoing risk by setting the timing of LV pacing to ensure that an end of IACI-LV$_{PROX}$ precedes the first heart sound S1 for LV contraction. More specifically, the PV and/or AV delay for LV pacing is set such that the LV is paced at or after both of the end of IACI-LV$_{PROX}$ and the first heart sound S1. The PV delay and/or AV delay is set to equal the sum of the IACI-LV$_{PROX}$ and a percentage (%) of the S1-conduction lag (PVD or AVD IACI-LV$_{PROX}$+%8ΔS1_C), where ΔS1_C is the S1-conduction lag from the end of IACI-LV$_{PROX}$ to the first heart sound S1 and the percentage (%) is less than 100%. Many HF patients have left bundle branch block (LBBB) which results in slow LV conduction, chronotropic incompetence, beta block and/or other physiologic behavior. When a patient experiences LBBB, a contraction of the left ventricle may be delayed in a manner such that the first heart sound S1 occurs after conduction propagates from the SA node to a proximal segment of the LV. Embodiments herein tailor operation to an HF patient's needs during exercise by, among other things, measuring and storing changes in PR, IACI-LV$_{PROX}$, ΔS1_C lag, and intrinsic heart rate from rest to different activity levels.

Additionally, or alternatively, the methods and devices are further configured to switch from the BiV pacing therapy to a left univentricular (LV only) pacing therapy that delivers pacing stimulation at one or more left ventricular sites and does not deliver any pacing stimulation to any right ventricular sites when the S1 heart sound occurs before the IACI-LV$_{PROX}$ and/or the patient is in an active exercise state. Additionally, or alternatively, the methods and devices are further configured to identify a patient active state and set the AV delay based on the IACI-LV$_{PROX}$, only when a patient is in the patient active state.

Implantable Medical Device

Figure 2:
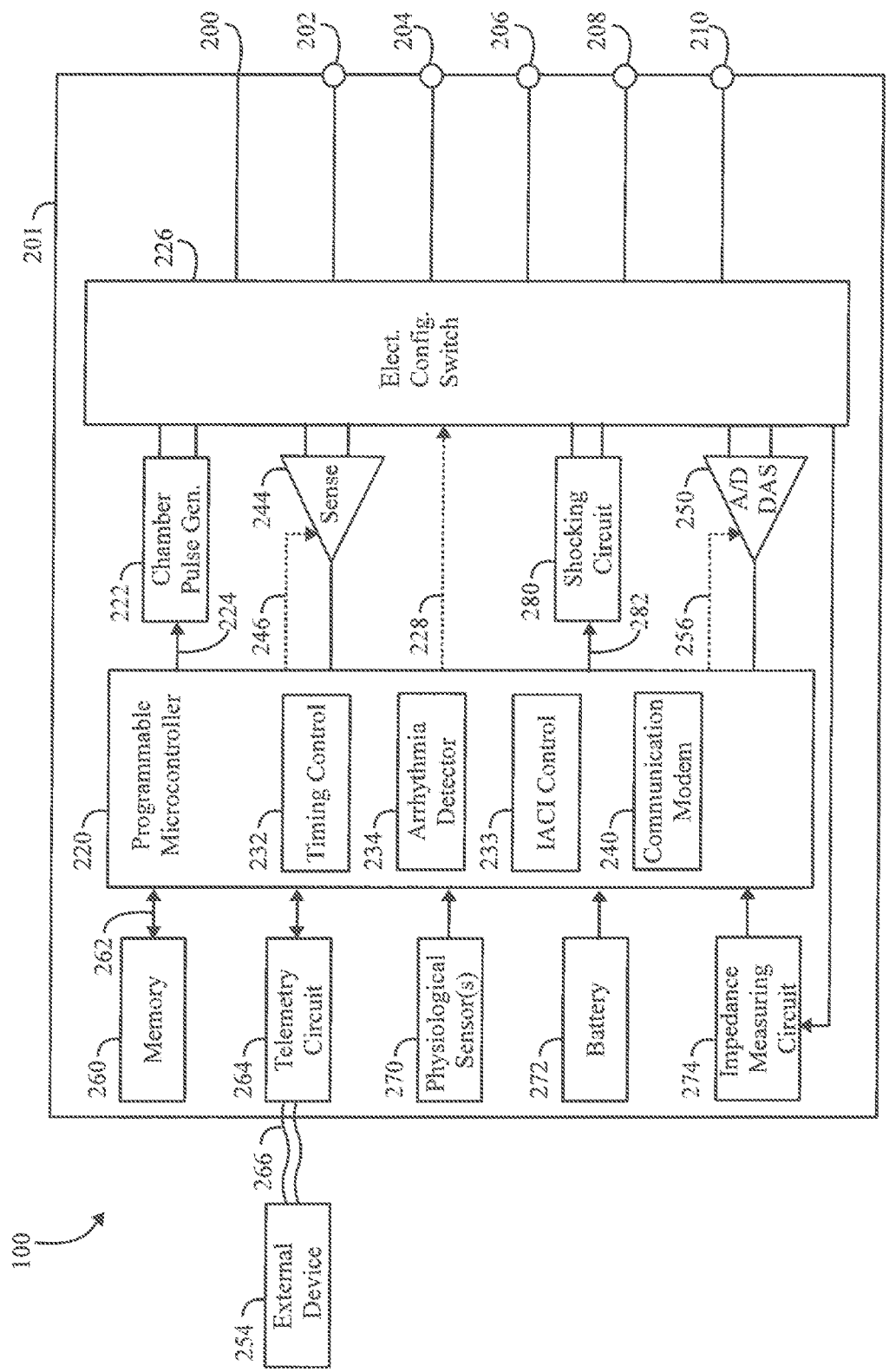
FIG. 2 shows a block diagram of an exemplary IMD that is implanted into the patient as part of the implantable cardiac system in accordance with embodiments herein.

FIG. 2 shows a block diagram of an exemplary ND 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the ND 100 may provide full-function cardiac resynchronization therapy. Alternatively, the ND 100 may be implemented with a reduced set of functions and components. For instance, the IMD may be implemented without ventricular sensing and pacing. As described herein, the IMD 100 is configured to provide LUV pacing therapy without pacing the RV.

The IMD 100 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals 202, 204, 206, 208, and 210. The terminals may be connected to electrodes that are located in various locations within and about the heart. For example, the terminals may include: a terminal 202 to be coupled to an first electrode (e.g., a tip electrode) located in a first chamber; a terminal 204 to be coupled to a second electrode (e.g., tip electrode) located in a second chamber; a terminal 206 to be coupled to an electrode (e.g., ring) located in the first chamber; a terminal 208 to be coupled to an electrode located (e.g., ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. Microcontroller 220 includes a microprocessor (or equivalent control circuitry), RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

In the example of FIG. 2, a single pulse generator 222 is illustrated. Optionally, the IMD 100 may include multiple pulse generators, similar to pulse generator 222, where each pulse generator is coupled to one or more electrodes and controlled by the microcontroller 220 to deliver select stimulus pulse(s) to the corresponding one or more electrodes.

Microcontroller 220 is illustrated to include timing control circuitry 232 to control the timing of the stimulation pulses (e.g., pacing rate, atrio-ventricular (AV) delay, atrial interconduction (A-A) delay, or ventricular interconduction (V-V) delay, etc.). In connection with embodiments herein, the timing control circuitry 232 is used to manage an LV atrial-ventricular ($AV_{LV}$) delay that is set as described herein to support LUV pacing therapy. The timing control circuitry 232 may also be used for the timing of refractory periods, blanking intervals, noise detection windows, evoked response windows, alert intervals, marker channel timing, and so on. Microcontroller 220 also has an arrhythmia detector 234 for detecting arrhythmia conditions and a morphology detector to review and analyze one or more features of the morphology of cardiac signals.

The microcontroller 220 includes an IACI control circuitry 233 to implement the processes described herein for controlling a pacing therapy. The IACI control circuitry 233 is configured to obtain an intra-atrial conduction interval (IACI-$LV_{PROX}$) between an atrial event and intrinsic conduction at an LV site that is proximal to an sinoatrial (SA) node and obtain timing of a first heart sound S1. The IACI control circuitry 233 is configured to determine whether the S1 occurs after the IACI-$LV_{PROX}$. By way of example, the IACI control circuitry 233 is further configured to determine whether a select point in the S1 occurs after an end of the IACI-$LV_{PROX}$. The select point determined by the IACI control circuitry 233 corresponds to the timing of mitral valve closure.

The IACI control circuitry 233 is configured to calculate an S1-conduction lag $\Delta S1\_C$ between the IACI-$LV_{PROX}$ and the first heart sound S1. The IACI control circuitry 233 is configured to set an atrial-ventricular pacing (AV) delay based on the IACI-$LV_{PROX}$ and the $\Delta S1\_C$. By way of example, the AV delay may be based on a sum of the IACI-$LV_{PROX}$ and a percentage (%) of the $\Delta S1\_C$ as follows: AV delay=IACI-$LV_{PROX}$+%*$\Delta S1\_C$. The foregoing equation enables the AV delay to be set based on the $\Delta S1\_C$ in a manner to avoid delivering a ventricular pacing pulse of a pacing therapy based on the AV delay before a mitral valve closes between the LV and left atrium. In addition, the IACI control circuitry 233 is configured to set the AV delay independent of the S1 conduction lag $\Delta S1\_C$ when the first heart sound S1 occurs before the end time of the IACI-$LV_{PROX}$. Optionally, the IACI control circuitry 233 may be further configured to measure a pacing latency PL between a paced event, delivered at the LV site, and an evoked response, sensed at the LV site; and subtract the PL from the AV delay.

The IACI control circuitry 233 is configured to deliver a pacing therapy based on the AV delay. For example, the IACI control circuitry 233 may be configured to deliver a biventricular (BiV) pacing therapy. The IACI control circuitry 233 is configured to switch from the BiV pacing therapy to a left univentricular pacing therapy that delivers pacing stimulation at one or more left ventricular sites and does not deliver any pacing stimulation to any right ventricular sites when the first heart sound S1 occurs before the end time of the IACI-$LV_{PROX}$. Additionally, or alternatively, the IACI control circuitry 233 may be configured to identify a patient active state and perform the setting operation only when in the patient active state.

The memory 260 is configured to store $AV_{LV}$ delay that is set by the microcontroller 220 based on an interventricular pacing (VV) delay that is set based on the following: VV=FCTR($\Delta*W_1+\epsilon*W_2+PL*W_3$), where FCTR is any desired non-zero number, and $W_1$ to $W_3$ represent weighting factors. The microcontroller 220 determines the atrial-ventricular conduction delay ($AR_{RV}$) between the A site and the RV site; and sets the $AV_{LV}$ delay based on a difference between the $AR_{RV}$ and the VV delay. The microcontroller 220 measures the pacing latency PL by measuring a latency interval between a paced event, delivered at the LV site, and an evoked response, sensed at the LV site. The microcontroller 220 compares the pacing latency with a threshold and adjusts the VV delay based on the comparison. The microcontroller 220 sets the interventricular pacing delay VV delay based on the conduction difference A and the correction term $\epsilon$, and not the pacing latency PL when a difference between the IACD and $AR_{LV}$ exceeds a threshold.

Although not shown, the microcontroller 220 may further include other dedicated circuitry and/or firmware/software components that assist in monitoring various conditions of the patients heart and managing pacing therapies. The microcontroller 220 manages feedback to confirm the LUV pacing therapy. The microcontroller 220 uses at least one of QRS related feedback, mechanical di-synchrony related feedback or stroke volume surrogate related feedback. For example, the microcontroller 220 may analyze a paced QRS width in connection with multiple $AV_{LV}$ delays, and select an $AV_{LV}$ delay corresponding to the paced QRS width having a criteria of interest. Optionally, the microcontroller 220 may analyze a contractility time delay in connection with multiple $AV_{LV}$ delays, and select an $AV_{LV}$ delay corresponding to the contractility time delay having a criteria of interest. Optionally, the microcontroller 220 may analyze a stroke volume impedance in connection with multiple $AV_{LV}$ delays, and select an $AV_{LV}$ delay corresponding to the stroke volume impedance having a criteria of interest.

The IMD 100 is further equipped with a communication modem (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 includes sensing circuit 244 selectively coupled to one or more electrodes that perform sensing operations, through the switch 226 to detect the presence of cardiac activity in the right chambers of the heart. The sensing circuit 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD 100 to sense low amplitude signal characteristics of atrial fibrillation. Switch 226 determines the sensing polarity of the cardiac signal by selectively closing the appropriate switches. In this way, the clinician may program the sensing polarity independent of the stimulation polarity.

The output of the sensing circuit 244 is connected to the microcontroller 220 which, in turn, triggers or inhibits the pulse generator 222 in response to the absence or presence of cardiac activity. The sensing circuit 244 receives a control signal 246 from the microcontroller 220 for purposes of controlling the gain, threshold, polarization charge removal circuitry (not shown), and the timing of any blocking circuitry (not shown) coupled to the inputs of the sensing circuit.

In the example of FIG. 2, a single sensing circuit 244 is Illustrated. Optionally, the IMD 100 may include multiple sensing circuit, similar to sensing circuit 244, where each sensing circuit is coupled to one or more electrodes and controlled by the microcontroller 220 to sense electrical activity detected at the corresponding one or more electrodes. The sensing circuit 244 may operate in a unipolar sensing configuration or in a bipolar sensing configuration.

The IMD 100 further includes an analog-to-digital (A/D) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The operating parameters of the MVO 100 may be non-invasively programmed into the memory 260 through a telemetry circuit 264 in telemetric communication via communication link 266 with the external device 254. The telemetry circuit 264 allows intracardiac electrograms and status information relating to the operation of the IMD 100 (as contained in the microcontroller 220 or memory 260) to be sent to the external device 254 through the established communication link 266.

The IMD 100 can further include magnet detection circuitry (not shown), coupled to the microcontroller 220, to detect when a magnet is placed over the unit. A magnet may be used by a clinician to perform various test functions of the unit 200 and/or to signal the microcontroller 220 that the external programmer 254 is in place to receive or transmit data to the microcontroller 220 through the telemetry circuits 264.

The IMD 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. The microcontroller 220 responds by adjusting the various pacing parameters (such as rate, AV Delay, V-V Delay, etc.) at which the atrial and ventricular pacing pulses are administered. While shown as being included within the unit 200, the physiologic sensor(s) 270 may be external to the unit 200, yet still be implanted within or carded by the patient. Examples of physiologic sensors might include sensors that, for example, sense respiration rate, pH of blood, ventricular gradient, activity, position/posture, minute ventilation (MV), and so forth.

A battery 272 provides operating power to all of the components in the IMC 100. The battery 272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the unit 200 employs lithium/silver vanadium oxide batteries.

The IMD 100 further includes an impedance measuring circuit 274 that is enabled by the microcontroller 220 via a control signal 282.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 211 to 40 joules), as controlled by the microcontroller 220. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Figure 3:
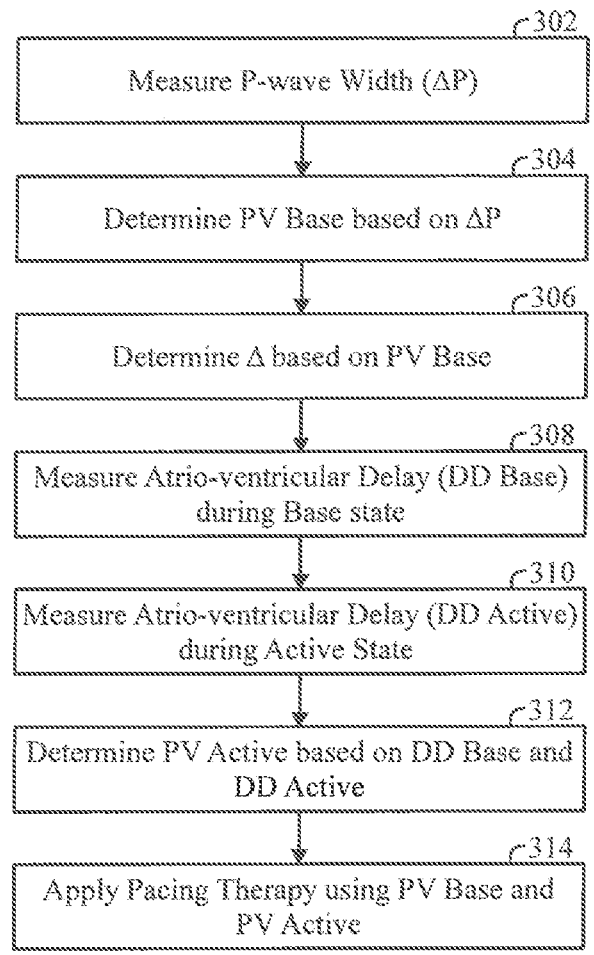
FIG. 3 illustrates a process for managing pacing parameters in connection with rate adaptive cardiac resynchronization therapy in accordance with embodiments herein.

FIG. 3 illustrates a process for managing pacing parameters in connection with rate adaptive cardiac resynchronization therapy in accordance with embodiments herein. All or a portion of the operations of FIG. 3 may be performed by one or more processors of an IMD, an external device, a server operating on a medical network and the like. The operations of FIG. 3 may be implemented in combination with the systems and methods described in U.S. Pat. No. 7,778,706, titled "Rate Adaptive Biventricular and Cardiac Resynchronization Therapy" (the '706 Patent) and/or U.S. Pat. No. 7,702,390, titled "Rate Adaptive Biventricular and Cardiac Resynchronization Therapy" (the '390 Patent), the complete subject matter both of which are incorporated herein by reference.

At 302, the one or more processors measure a P wave width (ΔP base) during a patient base state. Optionally, at 302, the processors may determine $IACI-LV_{PROX}$ and $\Delta S1\_C$ (as described in connection with FIG. 4) and utilize $IACI-LV_{PROX}$ and $\Delta S1\_C$ in combination with, or in pace of, P-wave width (ΔP base) in the following operations of FIG. 3. At 304, the one or more processors determine a patient base state PV delay (PV base) based on the P wave width (ΔP base). At 306, the one or more processors determine a value of a parameter Δ wherein the value of the parameter Δ depends on the P wave width (ΔP base) and/or based on $IACI-LV_{PROX}$ and $\Delta S1\_C$. At 308, the one or more processors measure an atrio-ventricular delay (DD base) during the patient base state. At 310, the one or more processors measure an atria-ventricular delay (OD active) during a patient active state.

At 312, the one or more processors determine a patient active state PV delay (PV active) based at least in part on the atrio-ventricular delay (DD base) and the atrio-ventricular delay (DD active) wherein the atrio-ventricular delays extend from the end of a respective P wave to the beginning of a respective ventricular QRS complex or a select point within a respective ventricular QRS complex. Optionally, the processors may determine the PV active for pacing the left ventricle and for pacing the right ventricle. At 314, the one or more processors apply a pacing therapy that uses PV base or PV active. Optionally, at 314, the one or more processors may sense patient activity and utilized the sensed patient activity to select between the PV base or the PV active for use with the pacing therapy.

Figure 4:
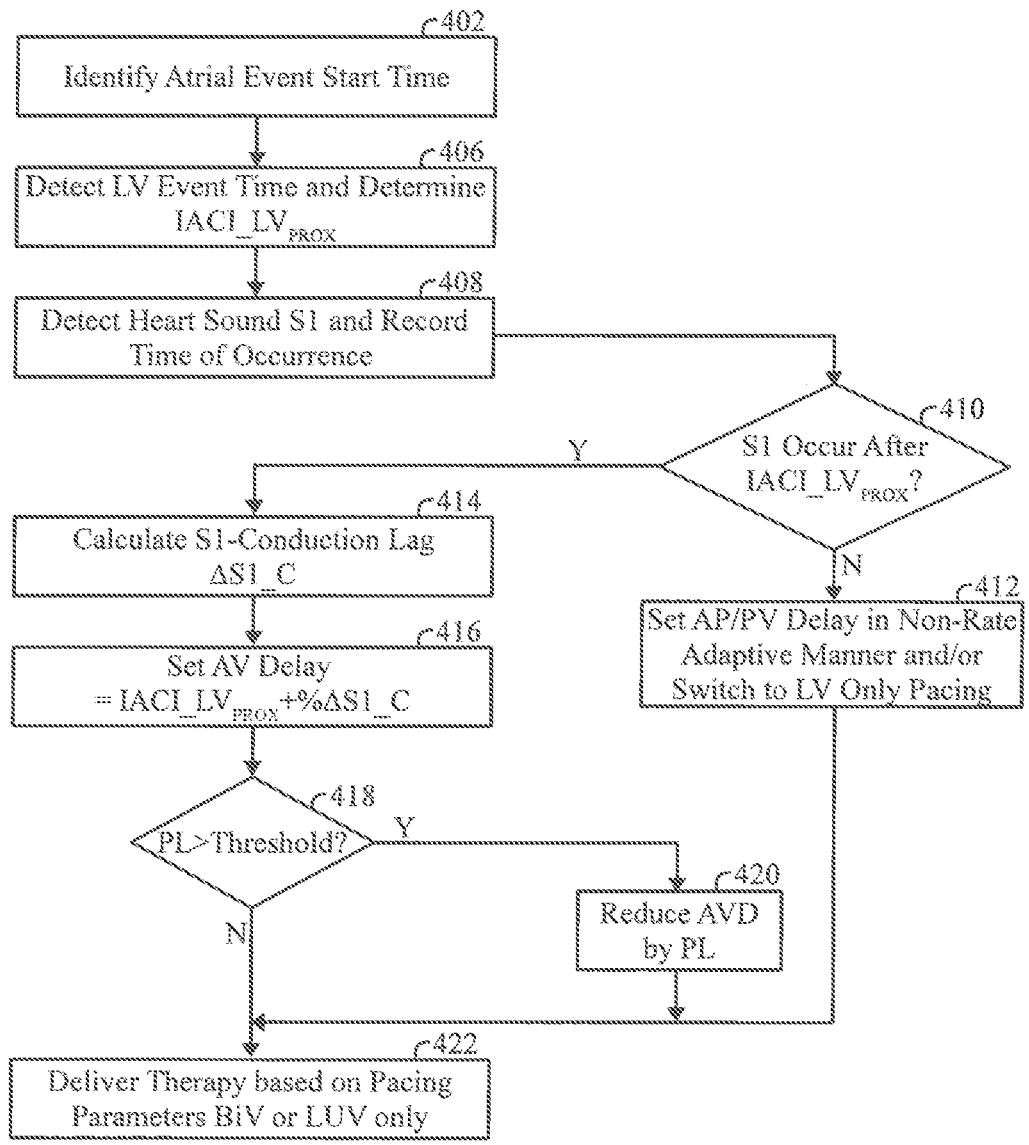
FIG. 4 illustrates a process to adjust the pacing parameters to avoid undesired pacing in connection with HF patients that exhibit LBBB or certain other abnormal physiologic behavior during exercise, in accordance with embodiments herein.

Following or in parallel with the operations of FIG. 3, embodiments herein implement the process of FIG. 4 (as described hereafter) to determine when and how much to further refine the pacing parameters. Optionally, the operations of FIG. 3 may be omitted entirely and the operations of FIG. 4 may be performed independently and as a stand-alone process to manage pacing parameters.

FIG. 4 illustrates a process to adjust the pacing parameters to avoid undesired pacing in connection with HF patients that exhibit LBBB or certain other abnormal physiologic behavior during exercise, in accordance with embodiments herein. As one example, the process of FIG. 4 avoids pacing at a time that would cause the left ventricle to push blood from the LV back into the left atria (LA). Embodiments herein avoid the foregoing risk by setting the timing of LV pacing to ensure that an end of $IACI-LV_{PROX}$ precedes the first heart sound S1 for LV contraction. More specifically, the PV and/or AV delay for LV pacing is set such that the LV is paced i) at or after the end of $IACI-LV_{PROX}$ and ii) before the first heart sound S1. All or a portion of the operations of FIG. 4 may be performed by one or more processors of an IMD, an external device, a server operating on a medical network and the like. Optionally, the operations of FIG. 4 may be implemented in combination with the systems and methods described In either or both of the '706 and '390 Patents.

At 402, one or more processors identify an atrial (A) event. For example, the A event may be an intrinsic or paced atrial event. When an atrial event is identified, the processors start one or more timers. Optionally, a dock may continuously run and, when the atrial event is detected, the processors record the current time of the atrial event from the running dock.

At 406, the one or more processors obtaining an intra-atrial conduction interval ($IACI-LV_{PROX}$) between an atrial event and intrinsic; conduction at an LV site that is proximal to a sinoatrial (SA) node. In certain embodiments, the LV lead includes multiple LV electrodes, each of which defines an LV sensing site. Depending on LV lead placement, tissue health, heart shape, etc., different LV sites in different patients may be the most physically proximate LV site to the SA node and/or may be the first LV sensing site to detect the intrinsic event propagating from the atrium. The processors may monitor one or more LV sensing sites for an intrinsic LV event. The processors record a time of the LV event and based thereon determine an intra-atrial conduction interval ($IACI-LV_{PROX}$) between the A site and the proximal or first LV site to sense conduction following the event at the A site. The term "proximal" may refer to a point in time or a physical relation. For example, the proximal LV site may be chosen as the LV electrode on the LV lead that is physically proximal to the SA node relative to a physical location of the other LV electrodes. Alternatively, the proximal LV site may be chosen as the LV electrode that is first in time, from all of the LV electrodes, to detect an intrinsic evoked response following the paced or sensed atrial event. The $IACI-LV_{PROX}$ may be recorded as a current time of a timer that was started when the atrial event was identified. Additionally, or alternatively, when using a running dock, the processors may determine the $IACI-LV_{PROX}$ as a time interval between a start time (recorded at 402), and an end time recorded when the first LV site detects the intrinsic event.

408, the one or more processors obtaining timing of a first heart sound S1. For example, the processors detect a first heart sound S1 and record the time at which the first heart sound S1 occurred. By way of example, a second timer (e.g., an S1 timer) may be activated when a paced or sensed event is identified in the atrium. The timer continues to operate until the first heart sound S1 is detected. Once the first heart sound S1 is detects, the S1 timer is stopped and the time is recorded as the S1 timing. Additionally, or alternatively, the processors may utilize the same running clock to record a current time for the end of the $IACI-LV_{PROX}$ and the first heart sound S1. The processors may Identify the timing of the first heart sound S1 as a start point, center or end point of the S1 signal. Optionally, the processors may determine a select point in the S1 occurs, such as a first positive peak 550 (FIG. 5) of the S1 heart sound which generally corresponds to mitral valve closure.

At 410, the one or more processors determine whether the first heart sound S1 occurs after the intrinsic event at the first LV sensing site. For example, the processors may determine whether a timing of the S1 occurs before, at or after an end of the $IACI-LV_{PROX}$. When the first heart sound S1 occurs before the end of the $IACI-LV_{PROX}$, flow moves to 412. At 412, the one or more processors determine the AV delay based on the process of FIG. 3. When the first heart sound S1 occurs before the end of the $IACI-LV_{PROX}$, the method avoids setting an AV delay for pacing in a rate adaptive manner based on S1. Instead, the AV delay may be set (independent of the S1-conduction lag ΔS1_C) based on non-rate adaptive techniques described in the 706 and '390 patents. Additionally, or alternatively, the processors may switch to an LV only pacing mode. Additionally, or alternatively, at 412, the processors may determine and utilize a width of the P-wave ΔP, a parameter β, and the interval DD, for example based on the processes described in the '706 Patent and/or the '390 Patent. When flow advances from 410 to 412 to 422, the process sets the AV delay independent of the S1-conduction lag ΔS1_C. The AV delay can be set independent of the S1 conduction lag ΔS1_C when the first heart sound S1 occurs before the end time of the IACI-$LV_{PROX}$, and thus the mitral valve is expected to close before the AV delay would expire in a subsequent cardiac cycle.

Alternatively, at 410, when the first heart sound S1 occurs at or after the $LV_{PROX}$, flow moves to 414. At 414, the one or more processors calculate an S1-conduction lag ΔS1_C between the IACI-$LV_{PROX}$ and the first heart sound S1 based on the IACI-$LV_{PROX}$. For example, the lag S1-conduction lag ΔS1_C is determined as a difference between i) an end timing of the IACD, and ii) an occurrence of the first heart sound S1 (ΔS1_C=$LV_{PROX-S}$1). Optionally, the S1 conduction lag ΔS1_C may be based on a weighted combination of the IACD timing and the S1 timing (e.g., a weighted difference).

At 416, the one or more processors set the AV delay based on the IACI-$LV_{PROX}$ and the ΔS1_C. For example, the AV delay may be set based on a sum of the IACI-$LV_{PROX}$ and the ΔS1_C as follows: AV delay=IACI-$LV_{PROX}$+%ΔS1_C, where the percentage % is predetermined to define a percentage of the S1-conduction lag to add to the IACI-$LV_{PROX}$. The percentage %ΔS1_C added to the AV delay is set to avoid delivering a ventricular pacing pulse of a pacing therapy before a mitral valve closes between the LV and left atrium.

Optionally, at 416, the processors may set the PV delay to be the same as or different from the AV delay. For example, when different AV and PV delays are to be used, the PV delay may be set based on a sum of the IACI-$LV_{PROX}$ and a second percentage (% 2) of the ΔS1_C as follows: AV delay IACI-$LV_{PROX}$+%$_2$*ΔS1_C, where the percentage %$_2$ is predetermined and differs from the percentage of the S1-conduction lag utilized when setting the AV delay.

At 418, the one or more processors may measure a pacing latency (PL) at the proximal LV site. For example, the pacing latency PL is measured by measuring a latency interval between a paced event delivered at the proximal LV site and an evoked response sensed at the same proximal LV site. The PL measurement may be performed at any time independent of, separate from and/or in parallel with, the other operations described herein. For example, pacing latency may be determined at any point within delivery of a pacing therapy, such as following any LV pacing event. The pacing latency may be recorded for future use. At 418, the one or more processors determine whether the pacing latency equals or exceeds a threshold. The threshold may be programmed by a clinician, or set automatically by the IMD based on feedback obtained during operation. By way of example, the threshold may be 5 msec, 10 msec, etc. Optionally, the threshold may be dynamically adjusted based on the patient's physiologic behavior, such as the resting heart rate, current heart rate, activity level, and the like.

When the pacing latency equals or exceeds the threshold, flow moves to 420. At 420, the one or more processors adjust the AV delay and/or PV delay by the PL. For example, 420, the one or more processors reduce the AV delay by a value of the PL or by a weighted value of the pacing latency. Returning to 418, when the pacing latency does not exceed the threshold, flow moves to 422.

At 422, the one or more processors deliver a pacing therapy based on various pacing parameters, including the AV delay and/or PV delay set in accordance with the operations of FIG. 4. For example, the one or more processors are configured to deliver a biventricular (BiV) pacing therapy. The one or more processors are further configured to switch from the BiV pacing therapy to a left univentricular pacing therapy based on the timing of the S1 and IACI-$LV_{PROX}$. For example, the processors may deliver the LUV pacing stimulation at one or more left ventricular sites and not deliver any pacing stimulation to any right ventricular sites when the S1 occurs after an end of the IACI-$LV_{PROX}$. It is recognized that the pacing therapy determined in accordance with the operations of FIG. 3 may perform atrial pacing.

The operations of FIG. 4 may be performed each time the IMD recalculates the adaptive pacing rate. Optionally, the operations of FIG. 4 may be performed only when the patient is experiencing a select state, such as an active state or exercise state. For example, an initial determination may be made at or before 402 to determine whether the patient is in a patient active state. When the patient is not in the active state (e.g., instead is in a rest state), the operations of FIG. 4 may be skipped and the AV/PV delay may be set independent of the S1 conduction lag ΔS1_C.

Figure 5:
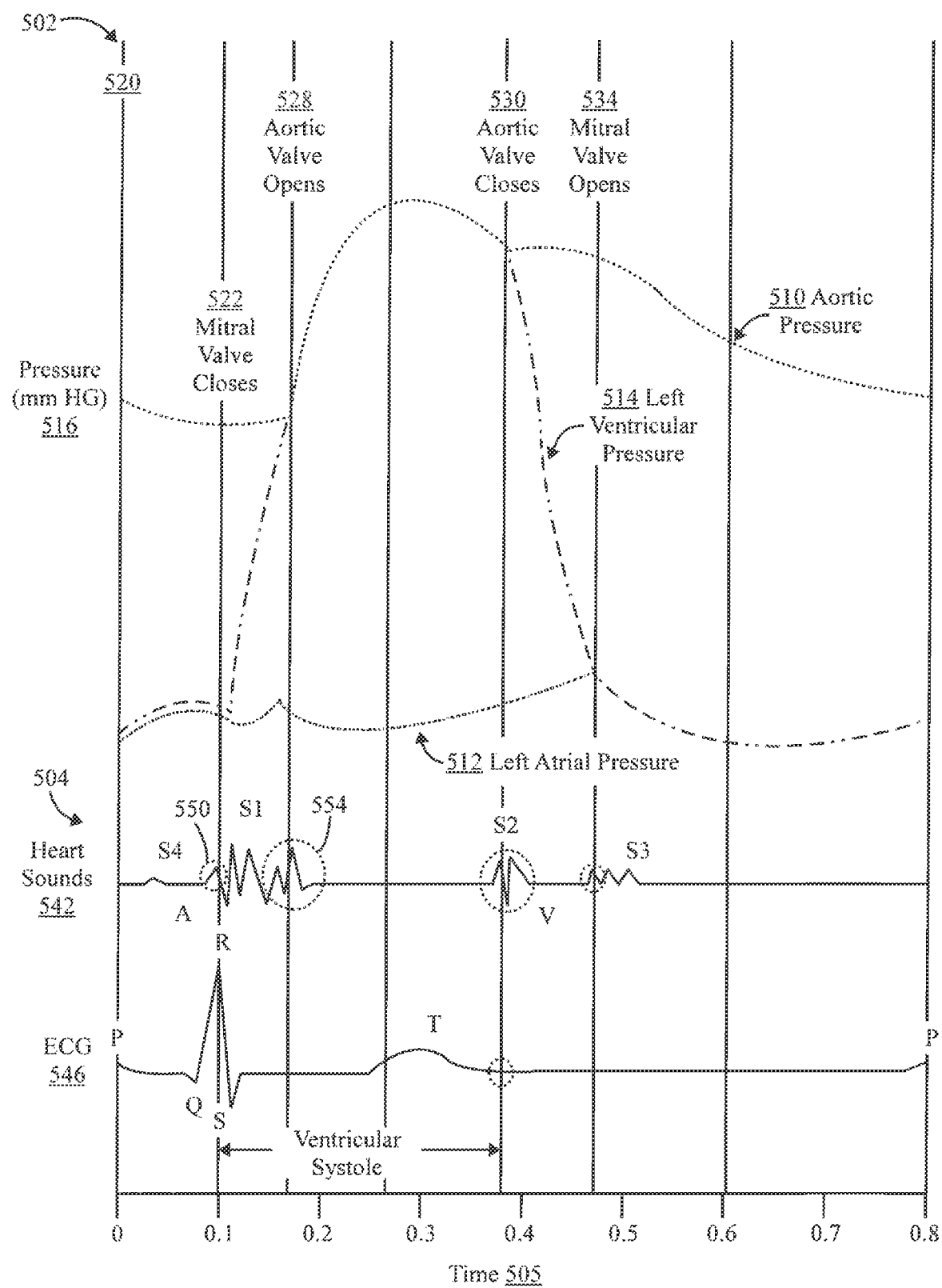
FIG. 5 illustrates an example anatomical diagram of certain parameters measured over a cardiac cycle.

FIG. 5 illustrates an example anatomical diagram of certain parameters measured over a cardiac cycle. Plot 502 represents blood pressure parameters, while plot 504 represents examples of heart sound and ECG parameters indicative of cardiac valve events. Both plots are illustrated in relation to time 505 along the horizontal or x-axis where the duration of time 505 represents one cardiac cycle lasting approximately 0.8 seconds. Plot 502 presents aortic pressure as dotted line 510, left atrial pressure as dashed line 512, and left ventricular pressure as line 514 (alternating dashes and dots). Pressure values for the aortic, left atrial, and left ventricle pressures are represented vertically along the y-axis as pressure in millimeter of mercury (mm HG) 516. For purposes of explanation, starting arbitrarily at the leftmost portion 520 of plot 502 assume that the patient's mitral valve is open and the aortic valve is closed. At this point in the cardiac cycle, the left atrium is contracting and the left ventricle is relaxed. During these conditions, blood is flowing freely from the left atrium into the left ventricle. Subsequently, the left ventricle begins to contract, and at about the same time, the mitral valve closes as indicated at 522. When looking specifically at left atrial pressure 512, hemodynamics indicates that for a period between point 520 and mitral valve closing 522 that blood pressures within the left atrium and the left ventricle are approximately equal.

Upon closure of the mitral valve at 522, the left atrium and left ventricle again form separate non-connected chambers and pressure within the left ventricle diverges from the pressure in the left atrium as the left ventricle contracts. Both the mitral valve leading into the left ventricle and the aortic valve leading out of the left ventricle are closed for a period known as isovolumic contraction. Continuing with plot 502, at point 528 the aortic valve leading from the left ventricle into the aorta opens. With the opening of the aortic valve, blood flows from the left ventricle into the aorta and pressures within the left ventricle and the aorta generally equalize. Pressure within the left ventricle and the aorta remain generally equal until the aortic valve closes at point 530. The closing of the aortic valve at 530 causes the left ventricle to be fluidly separated from the aorta. Subsequently, as the left ventricle relaxes its volume expands resulting in decreasing pressures within the left ventricle until the mitral valve opens at 534. Opening of the mitral valve at 534 occurs as blood is pumped into the left ventricle from the left atrium. After the mitral valve opens at 534 blood flows into the left ventricle from the left atrium and the pressures within the left ventricle and the left atrium generally equalize for a period extending between mitral valve opening 534 and the right side of the plot.

Plot 504 provides examples for detecting cardiac valve events related to the mitral and aortic valves. Parameter 542 relates to heart sound data and parameter 546 relates to electrocardiogram (ECG) data. Heart sound parameter 542 includes 4 distinct heart sounds indicated as S1, S2, S3, and S4. Heart sounds can be detected with various types of detection mechanisms. For instance, heart sounds can be sampled with accelerometers, microphones, and or pressure transducers, among others. The heart sound detection mechanisms can be positioned external to a patient or internally. The heart sound detection mechanism may be positioned internally the patient, such as within the housing of an IMD. Additionally, or alternatively, the heart sound detection mechanism can be positioned upon a lead that is positioned in the patient's vasculature or heart. The mitral valve closure corresponds to the S1 heart sound generally. Specifically, a first positive peak 550 of the S1 heart sound generally corresponds to mitral valve closure as evidenced along the vertical axis. Aortic valve opening 528 can be detected from the heart sound parameter 642 as a last peak 554 of heart sound S1.

Electrogram parameter 546 includes peaks or waves labeled as "P", "Q", "R", "S", and "T". Electrogram data can be detected with various mechanisms. One such mechanism is described in detail above in relation to FIGS. 1-2 for sensing internal electrogram data. Other mechanisms can sense electrogram data externally via one or more sensors positioned upon the patient's skin proximate the thorax.

In the example of FIG. 5, the heart behaves in a relatively normal physiologic manner and the heart sound S1 occurs after a peak of the QRS complex (and after the evoked response at the proximal LV site). However, as explained herein, patients with LBBB will experience certain abnormalities in the conduction pattern.

Figure 6:
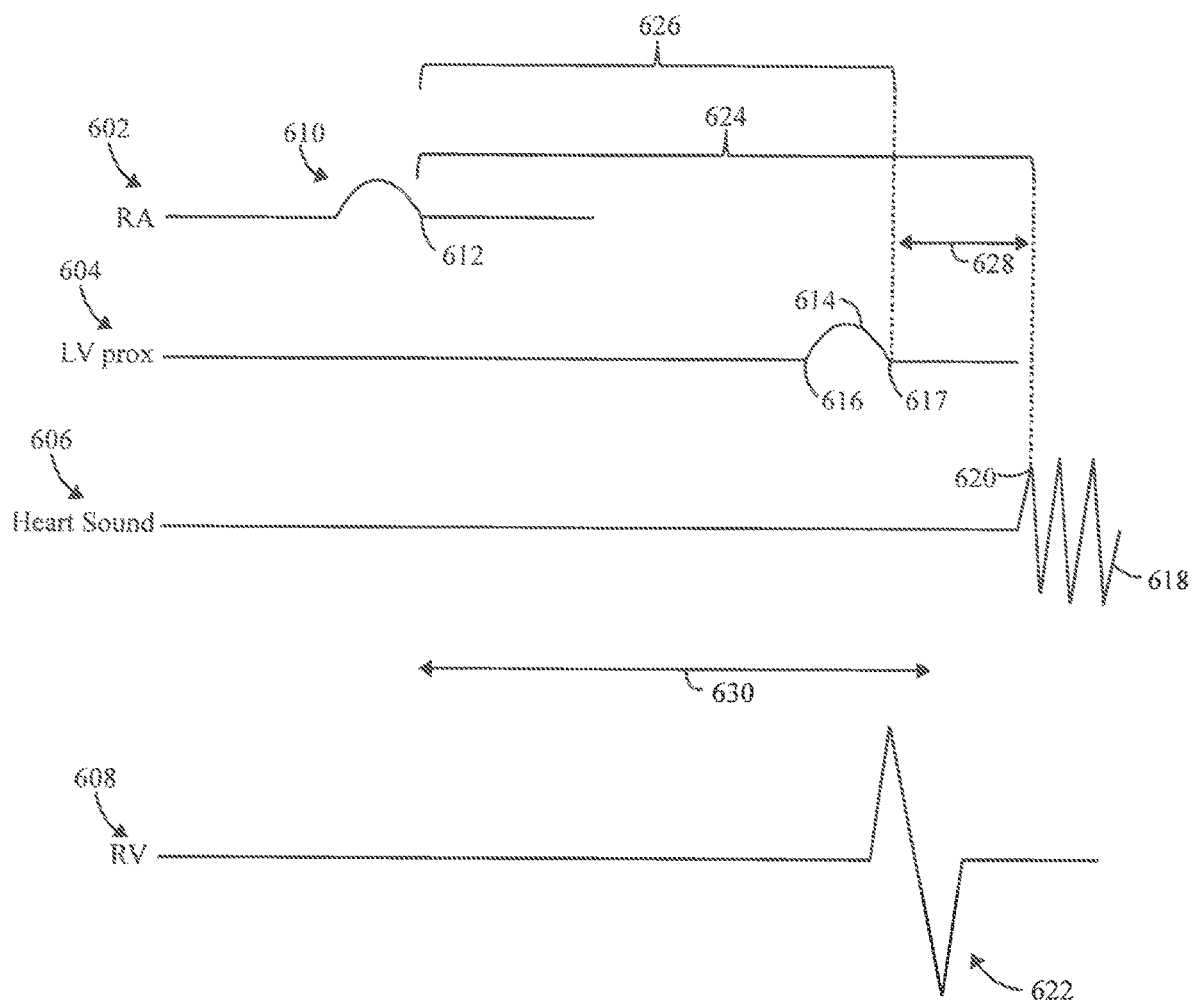
FIG. 6 illustrates an example abnormality in the conduction pattern such as for a patient with LBBB.

FIG. 6 illustrates an example conduction pattern. More specifically, FIG. 6 illustrates an atrial sensing channel 602, an LV sensing channel 604 corresponding to a proximal LV site, a heart sound sensing channel 606 and a right ventricular sensing channel 608. The atrial sensing channel 602 senses paced and intrinsic atrial events. The LV sensing channel 604 may be defined between the proximal LV electrode and another electrode, such as a RV electrode, a housing of the IMD, and the like. The heart sound sensing channel 606 includes any sounds detected by a sound sensor, such as an accelerometer in the IMD. The RV sensing channel 608 may be defined between one or more RV electrodes (e.g., a tip or ring electrode) and an RV coil electrode and/or a housing of the IMD.

In accordance with the operations of FIG. 4, the processors of the IMD detect, over the RA sensing channel, an atrial event (P wave) 610 and identify an end thereof at time 612. The processors detect, over the LV sensing channel 604, an intrinsic evoked response 614 and identify a beginning and end thereof at time 616 and 617. The processors detect, over the heart sound channel 606, a first heart sound 618 that includes a first peak at 620, while the RV sensing channel 608 detects a QRS complex 622. The processors determine the IACI-$LV_{PROX}$ 626 which is the interval between the end at time 612 of the atrial event 610 and the end at time 617 of the evoked response 614 at the proximal LV site. The processors identify the timing 624 to the peak 620 of the heart sound 618. The processors calculate the S1-conduction lag $\Delta S1\_C$ 628 from the end 617 of the response 617 to the first peak 620 of the first heart sound 618. The processors determine that the timing 624 of the heart sound 618 occurs after the end 617 of the IACI-$LV_{PROX}$ 626, and based thereon, the processors defines an AV delay 630 to equal a sum of the IACI-$LV_{PROX}$ 626 and a percentage/multiple of the S1-conduction lag $\Delta S1\_C$ 628.

Embodiments analyze numerous cardiac cycles, such as during exercise, to identify when the heart sound 618 follows or precedes the evoked response 614 at the proximal LV site. When the heart sound 618 follows the evoked response 614, the processors utilize the S1-conduction lag $\Delta S1\_C$ 628 to adjust the AV delay 630 to a patient's particular needs and avoid pacing the LV at a time that would otherwise push blood from the LV back through the mitral valve to the LA.

Figure 7:
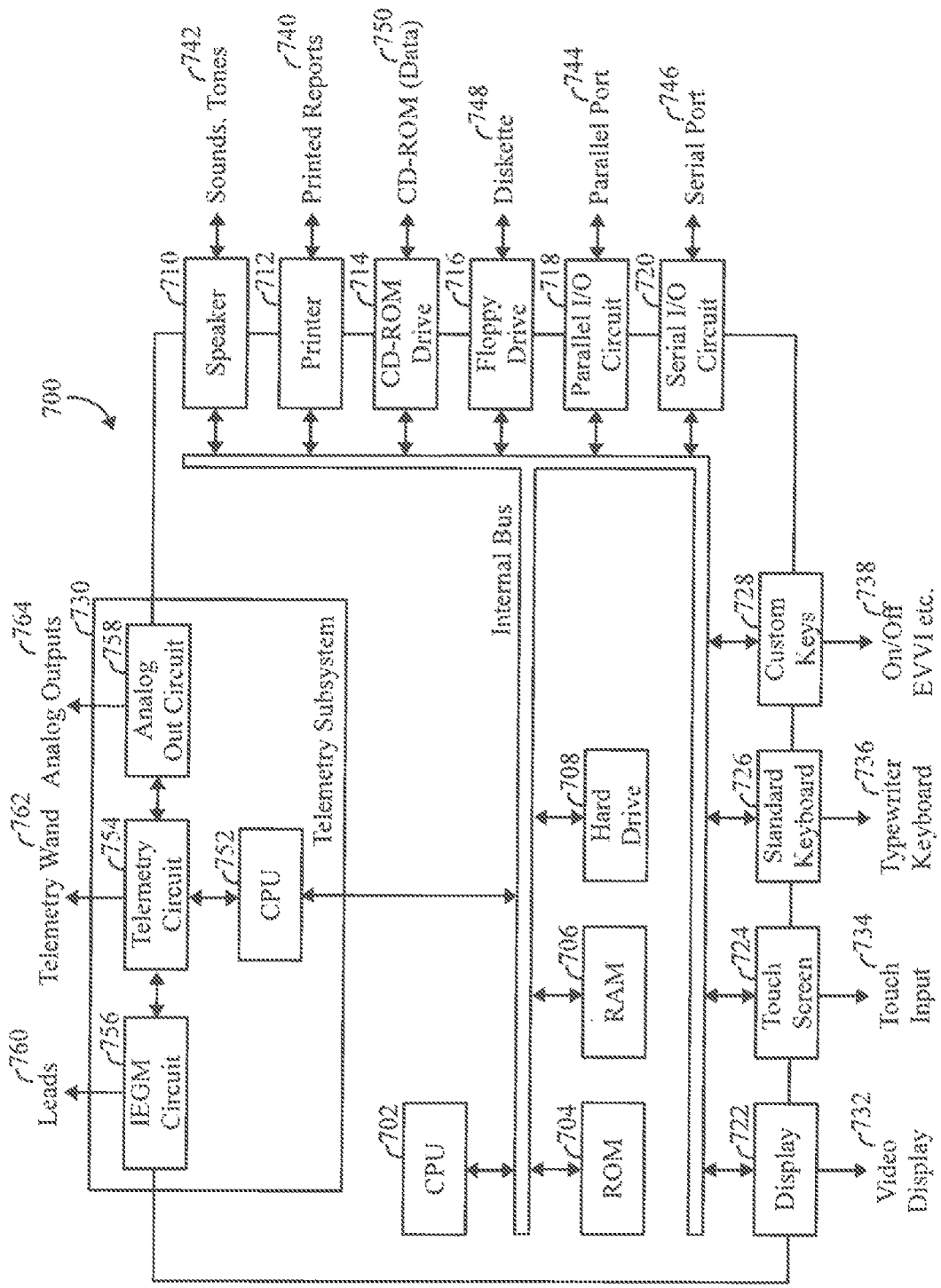
FIG. 7 illustrates a functional block diagram of the external device that is operated in accordance with the processes described herein and to interface with implantable medical devices as described herein.

FIG. 7 illustrates a functional block diagram of the external device 700 that is operated in accordance with the processes described herein and to interface with Implantable medical devices as described herein. The external device 700 may be a workstation, a portable computer, an IMD programmer, a PDA, a cell phone and the like. The external device 700 includes an internal bus that connects/interfaces with a Central Processing Unit (CPU) 702, ROM 704, RAM 706, a hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus is an address/data bus that transfers information between the various components described herein. The hard drive 708 may store operational programs as well as data, such as waveform templates and detection thresholds.

The CPU 702 typically includes a microprocessor, a microcontroller, or equivalent control circuitry, designed specifically to control interfacing with the external device 700 and with the IMD 100. The CPU 702 may include RAM or ROM memory, logic and timing circuitry, state machine circuitry, and I/O circuitry to interface with the IMD 100. The CPU 702 may implement some or all of the operations of the IACI control circuitry 233 (FIG. 2). The CPU 702 may implement some or all of the operations of the methods described herein.

The display 722 (e.g., may be connected to the video display 732). The touch screen 724 may display graphic information relating to the IMD 100. The display 722 displays various information related to the processes described herein. The touch screen 724 accepts a user's touch input 734 when selections are made. The keyboard 726 (e.g., a typewriter keyboard 736) avows the user to enter data to the displayed fields, as well as interface with the telemetry subsystem 730. Furthermore, custom keys 728 turn on/off 738 (e.g., EVVI) the external device 700. The printer 712 prints copies of reports 740 for a physician to review or to be placed in a patient file, and speaker 710 provides an audible warning (e.g., sounds and tones 742) to the user. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750.

The telemetry subsystem 730 includes a central processing unit (CPU) 752 in electrical communication with a telemetry circuit 754, which communicates with both an IEGM circuit 756 and an analog out circuit 758. The circuit 756 may be connected to leads 760. The circuit 756 is also connected to the implantable leads to receive and process IEGM cardiac signals as discussed above. Optionally, the IEGM cardiac signals sensed by the leads may be collected by the IMD 100 and then transmitted, to the external device 700, wirelessly to the telemetry subsystem 730 input.

The telemetry circuit 754 is connected to a telemetry wand 762. The analog out circuit 758 includes communication circuits to communicate with analog outputs 764. The external device 700 may wirelessly communicate with the IWO 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 700 to the IMD 100.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Rash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive. ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for controlling an adaptive pacing therapy using an implantable medical device (IMD), the method comprising:
   providing electrodes configured to be located proximate to an atrial (A) site, left ventricular (LV) site and right ventricular (RV) site of the heart;
   utilizing one or more processors to perform:
      obtaining an intra-atrial conduction interval (IACI-$LV_{PROX}$) between an atrial event and intrinsic conduction at an LV site that is proximal to an sinoatrial (SA) node;
      obtaining timing of a first heart sound S1;
      determining whether the S1 occurs after the IACI-$LV_{PROX}$;
      calculating an S1-conduction lag $\Delta S1\_C$ between the IACI-$LV_{PROX}$ and the first heart sound S1;
      setting an atrial-ventricular pacing (AV) delay based on the IACI-$LV_{PROX}$ and the $\Delta S1\_C$; and
      delivering a pacing therapy based on the AV delay.

2. The method of claim 1, wherein the AV delay is based on a sum of the IACI-$LV_{PROX}$ and a percentage (%) of the $\Delta S1\_C$ as follows: AV delay=IACI-$LV_{PROX}$+%*$\Delta S1\_C$.

3. The method of claim 1, wherein the determining, further comprises determining whether a select point in the S1 occurs after an end of the IACI-$LV_{PROX}$.

4. The method of claim 1, wherein the obtaining the timing of the S1 further comprises obtaining the timing of mitral valve closure based on the S1.

5. The method of claim 1, wherein the setting the AV delay based on the $\Delta S1\_C$ further comprises setting the AV delay to avoid delivering a ventricular pacing pulse of a pacing therapy based on the AV delay before a mitral valve closes between the LV and left atrium.

6. The method of claim 1, further comprising measuring a pacing latency PL between a paced event, delivered at the LV site, and an evoked response, sensed at the LV site; and subtracting the PL from the AV delay.

7. The method of claim 1, further comprising determining whether the first heart sound S1 occurs before or after the end time of the IACI-$LV_{PROX}$,
   wherein the setting further comprises:
      i) setting the AV delay based on the IACI-$LV_{PROX}$ and the $\Delta S1\_C$, when the first heart sound S1 occurs after the end time of the IACI-$LV_{PROX}$, and
      ii) setting the AV delay in either: i) a non-rate adaptive manner or ii) an LV only pacing mode, when the first heart sound S1 occurs before the end time of the IACI-$LV_{PROX}$.

8. The method of claim 1, wherein the delivering the pacing therapy further comprises delivering a biventricular (BiV) pacing therapy.

9. The method of claim 8, further comprising switching from the BiV pacing therapy to a left univentricular pacing therapy that delivers pacing stimulation at one or more left ventricular sites and does not deliver any pacing stimulation to any right ventricular sites when the first heart sound S1 occurs before the end time of the IACI-$LV_{PROX}$.

10. The method of claim 1, further comprising identifying a patient active state and performing the setting operation only when in the patient active state.

11. A system controlling an adaptive pacing therapy using an implantable medical device (IMD), the system comprising:
   electrodes configured to be located proximate to an atrial (A) site, left ventricular (LV) site and right ventricular (RV) site of the heart;
   memory to store program instructions;
   one or more processors configured to implement the program instructions to perform:
      obtaining an intra-atrial conduction interval (IACI-$LV_{PROX}$) between an atrial event and intrinsic conduction at an LV site that is proximal to an sinoatrial (SA) node;
      obtaining timing of a first heart sound S1;
      determining whether the S1 occurs after the IACI-$LV_{PROX}$;
      calculating an S1-conduction lag $\Delta S1\_C$ between the IACI-$LV_{PROX}$ and the first heart sound S1;
      setting an atrial-ventricular pacing (AV) delay based on the IACI-$LV_{PROX}$ and the $\Delta S1\_C$; and
      delivering a pacing therapy based on the AV delay.

12. The system of claim 11, wherein the AV delay is based on a sum of the IACI-$LV_{PROX}$ and a percentage (%) of the $\Delta S1\_C$ as follows: AV delay=IACI-$LV_{PROX}$+%*$\Delta S1\_C$.

13. The system of claim 11, wherein the one or more processors is further configured to determine whether a select point in the S1 occurs after an end of the IACI-$LV_{PROX}$.

14. The system of claim 11, wherein the one or more processors is further configured to obtain the timing of mitral valve closure based on the S1.

15. The system of claim 11, wherein the one or more processors is further configured to set the AV delay based on the $\Delta S1\_C$ in a manner to avoid delivering a ventricular pacing pulse of a pacing therapy based on the AV delay before a mitral valve closes between the LV and left atrium.

16. The system of claim 11, wherein the one or more processors is further configured to measure a pacing latency PL between a paced event, delivered at the LV site, and an evoked response, sensed at the LV site; and subtract the PL from the AV delay.

17. The system of claim 11, wherein the one or more processors is further configured to:
   determine whether the first heart sound S1 occurs before or after the end time of the IACI-$LV_{PROX}$;
   set the AV delay based on the IACI-$LV_{PROX}$ and the $\Delta S1\_C$, when the first heart sound S1 occurs after the end time of the IACI-$LV_{PROX}$, and
   set the AV delay in either: i) a non-rate adaptive manner or ii) an LV only pacing mode, when the first heart sound S1 occurs before the end time of the IACI-$LV_{PROX}$.

18. The system of claim 11, wherein the one or more processors is further configured to deliver a biventricular (BiV) pacing therapy.

19. The system of claim 18, wherein the one or more processors is further configured to switch from the BiV pacing therapy to a left univentricular pacing therapy that delivers pacing stimulation at one or more left ventricular sites and does not deliver any pacing stimulation to any right ventricular sites when the first heart sound S1 occurs before the end time of the IACI-$LV_{PROX}$.

20. The system of claim 11, wherein the one or more processors is further configured to identify a patient active state and perform the setting operation only when in the patient active state.

* * * * *